(12) United States Patent
Mitchell et al.

(10) Patent No.: US 12,195,916 B2
(45) Date of Patent: Jan. 14, 2025

(54) SMALL DIAMETER CABLE

(71) Applicant: Fort Wayne Metals Research Products Corp, Fort Wayne, IN (US)

(72) Inventors: Robert A. Mitchell, Huntington, IN (US); Mark S. Michael, Corunna, IN (US)

(73) Assignee: Fort Wayne Metals Research Products, LLC, Fort Wayne, IN (US)

( * ) Notice: Subject to any disclaimer, the term of this patent is extended or adjusted under 35 U.S.C. 154(b) by 941 days.

(21) Appl. No.: 16/498,142

(22) PCT Filed: Mar. 30, 2018

(86) PCT No.: PCT/US2018/025422
§ 371 (c)(1),
(2) Date: Sep. 26, 2019

(87) PCT Pub. No.: WO2018/183862
PCT Pub. Date: Oct. 4, 2018

(65) Prior Publication Data
US 2021/0102335 A1    Apr. 8, 2021

Related U.S. Application Data

(60) Provisional application No. 62/479,943, filed on Mar. 31, 2017.

(51) Int. Cl.
*D07B 1/06* (2006.01)
*A61B 1/005* (2006.01)

(52) U.S. Cl.
CPC ............ *D07B 1/062* (2013.01); *A61B 1/0057* (2013.01); *D07B 2201/1036* (2013.01);
(Continued)

(58) Field of Classification Search
CPC ............ D07B 1/062; D07B 2201/1036; D07B 2201/1084; D07B 2201/2039;
(Continued)

(56) References Cited

U.S. PATENT DOCUMENTS 2,396,734 A * 3/1946 Williams, Jr. ......... D07B 1/147
174/128.1
3,079,460 A * 2/1963 Grove ...................... H01B 5/08
174/128.1
(Continued)

FOREIGN PATENT DOCUMENTS

CN 102535214 7/2012
DE 102017101646 A1 * 8/2018 ............... D07B 1/02
(Continued)

OTHER PUBLICATIONS

International Search Report and Written Opinion dated Jun. 20, 2018 in corresponding International Application No. PCT/US2018/025422.
(Continued)

*Primary Examiner* — Grace Huang
(74) *Attorney, Agent, or Firm* — Faegre Drinker Biddle & Reath LLP

(57) ABSTRACT

A wire cable construct including a plurality of strands each made of a plurality of wire filaments, the strands and wire filaments arranged in a 37×7 configuration of 37 strands of 7 wire filaments each, with the strands arranged in four layers including a first, central layer of a single strand, a second layer of six strands, a third layer of twelve strands and a fourth, outermost layer of eighteen strands. The cable may have a small diameter for use in medical device applications, and the strand and wire element configuration allows the cable to carry high axial loads, minimizes bending stress when the cable is routed around a tight turn such
(Continued)

FIG. 3A as a small pulley, and minimizes torsion in the cable due to axial loading.

37 Claims, 10 Drawing Sheets

(52) U.S. Cl.
CPC ............... *D07B 2201/1044* (2013.01); *D07B 2201/1084* (2013.01); *D07B 2201/2009* (2013.01); *D07B 2201/2039* (2013.01); *D07B 2201/204* (2013.01); *D07B 2205/3028* (2013.01); *D07B 2205/3082* (2013.01); *D07B 2205/3085* (2013.01)

(58) Field of Classification Search
CPC ...... D07B 2201/204; D07B 2205/3028; D07B 2205/3082; D07B 2205/3085
USPC ......................................................... 57/213
See application file for complete search history.

(56) References Cited

U.S. PATENT DOCUMENTS

| | | | |
|---|---|---|---|
| 3,339,012 A * | 8/1967 | Hutchins, Jr. ............ | H01B 7/14 174/128.1 |
| 4,197,695 A * | 4/1980 | Hughes ................ | D07B 1/0673 156/433 |
| 4,219,995 A | 9/1980 | Tajima et al. | |
| 4,332,131 A * | 6/1982 | Palsky .................. | B60C 9/0007 57/213 |
| 4,651,513 A | 3/1987 | Dambre | |
| 4,947,636 A * | 8/1990 | Sinopoli ............. | D07B 1/0613 57/218 |
| 5,330,482 A * | 7/1994 | Gibbs ..................... | D07B 5/00 606/113 |
| 5,687,557 A * | 11/1997 | De Vos ................ | D07B 1/0613 57/214 |
| 6,023,026 A | 2/2000 | Funahashi et al. | |
| 6,363,703 B1 * | 4/2002 | Kolmes .................. | D02G 3/442 57/210 |
| 6,627,009 B1 | 9/2003 | Matsui et al. | |
| 7,036,298 B2 | 5/2006 | Honda | |
| 7,089,724 B2 * | 8/2006 | Black, III ............ | D07B 1/0693 57/213 |
| 7,138,582 B2 * | 11/2006 | Lessar .................... | A61N 1/056 174/126.1 |
| 7,191,585 B2 * | 3/2007 | Vanderbeken ............ | B66B 7/06 57/223 |
| 7,501,579 B2 | 3/2009 | Michael et al. | |
| 8,006,475 B2 * | 8/2011 | Aoyama ............... | B60C 9/2006 57/212 |
| 10,745,855 B2 * | 8/2020 | Jessup ....................... | D07B 1/04 |
| 2001/0025475 A1 * | 10/2001 | Ouchi .................. | D07B 1/0693 57/224 |
| 2004/0026178 A1 * | 2/2004 | Honda .................. | D07B 5/007 187/251 |
| 2010/0096162 A1 * | 4/2010 | Cerra ..................... | H01B 5/104 174/126.2 |
| 2012/0312444 A1 * | 12/2012 | Domingo ............... | D07B 1/062 152/556 |
| 2013/0096658 A1 | 4/2013 | Shan et al. | |
| 2015/0152593 A1 * | 6/2015 | Darda .................... | D07B 1/025 87/3 |
| 2016/0322125 A1 | 11/2016 | Kamoshida et al. | |
| 2019/0390403 A1 * | 12/2019 | Waterbury ............... | D07B 1/06 |
| 2020/0122972 A1 * | 4/2020 | Vanreyten ............... | B66B 7/062 |

FOREIGN PATENT DOCUMENTS

| | | | | |
|---|---|---|---|---|
| JP | 2002327381 A | | 11/2002 | |
| JP | 2003041493 A | | 2/2003 | |
| JP | 2003201688 A | | 7/2003 | |
| JP | 2004250827 A | * | 9/2004 | .......... D07B 1/0613 |
| JP | 2005248375 | | 9/2005 | |
| JP | 3827610 B2 | | 9/2006 | |
| JP | 3910377 B2 | | 4/2007 | |
| JP | 4064668 B2 | | 3/2008 | |
| JP | 2014077215 A | * | 5/2014 | .......... D07B 1/0613 |
| KR | 101769761 B1 | * | 8/2017 | .......... F03B 13/1885 |
| WO | 200661888 | | 6/2006 | |
| WO | WO-2006061888 A1 | * | 6/2006 | .......... D07B 1/0673 |
| WO | 200823434 | | 2/2008 | |
| WO | WO-2008023434 A1 | * | 2/2008 | ............. D07B 1/165 |

OTHER PUBLICATIONS

International Preliminary Report on Patentability received for PCT Patent Application No. PCT/US2018/025422, mailed on Oct. 10, 2019, 6 pages.

* cited by examiner

SMALL DIAMETER CABLE

CROSS-REFERENCE TO RELATED APPLICATION

The present application is a national phase filing under 35 U.S.C. § 371 of International Application No. PCT/US2018/025422, titled "SMALL DIAMETER CABLE," filed on Mar. 30, 2018, which claims the benefit of priority to U.S. Provisional Application No. 62/479,943, filed with the U.S. Patent and Trademark Office on Mar. 31, 2017, the entire disclosures of which are expressly incorporated herein by reference.

BACKGROUND

1. Field of the Disclosure

The present disclosure relates to multi-filament wire cable constructs and, in particular, relates to miniature scale or small diameter cables for use in medical device applications.

2. Description of the Related Art

Wire ropes or multi-filament cables are commonly used in applications where axial and/or tensile loads are transmitted along a tortuous path, for example, around one or more pulleys or sheaves. Wire ropes or cables may vary widely in size, from large applications such as material handling in heavy industries such as the steel and automotive industries, to miniature or small scale applications.

For example, in the robotic and surgical instrument endoscopy markets, reduction in the size of endoscopes and the components that articulate the endoscopes is desirable. However, the loads required for the application typically do not decrease with instrument size. On the contrary, smaller instruments demand smaller moment arms for manipulation, and consequently higher forces.

In modern surgical instruments, it is common that axial loads combined with bending over pulleys as small as 2-3 mm in diameter, for example, place very high stresses on the cables. Under high axial loads, for example, greater than 50% of axial breaking load, known wire rope or cable constructs typically exhibit low cycle life. In addition, considerable torsion of the wire rope may occur as the helical winding of the cable attempts to "unwind" under high tensile loads.

In some surgical instruments used in minimally invasive surgical procedures, for example, the total size of the instrument is limited by the human body. Such instruments may have a maximum transverse dimension of about 7-8 mm, and this dimension may preferably be smaller and may not be larger. This small maximum dimension is imposed by human physiology, i.e., the spaces between tissues and bones which cannot be violated by the surgical instrument.

What is needed is an improvement over the foregoing.

SUMMARY

The present disclosure provides a wire cable construct including a plurality of strands each made of a plurality of wire filaments, the strands and wire filaments arranged in a 37×7 configuration of 37 strands of 7 wire filaments each, with the strands arranged in four layers including a first, central layer of a single strand, a second layer of six strands, a third layer of twelve strands and a fourth, outermost layer of eighteen strands. The cable may have a small diameter for use in medical device applications, and the strand and wire element configuration allows the cable to carry high axial loads, minimizes bending stress when the cable is routed around a tight turn such as a small pulley, and minimizes torsion in the cable due to axial loading.

In one form thereof, the present invention provides a wire cable including 37 strands each including at least 7 wire filaments, each wire filament formed from a medical-grade material, the strands arranged in layers. The layer include a first, central layer of a single strand; a second layer of six strands; a third layer of twelve strands; and a fourth, outermost layer of eighteen strands. The wire filaments each have a diameter between 0.005 mm and 0.143 mm, and the wire cable has an outermost diameter between 0.11 mm and 3.0 mm.

In another form thereof, the present invention provides a medical device, including a least one pulley having a root diameter and a wire cable. The wire cable has 37 strands each including at least 7 wire filaments, the strands arranged in layers. The layers include a first, central layer of a single strand; a second layer of six strands; a third layer of twelve strands; and a fourth, outermost layer of eighteen strands. The wire cable has an outermost diameter between 0.11 mm and 3 mm, and the root diameter is between 3 and 6 times the outermost diameter of the wire cable.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
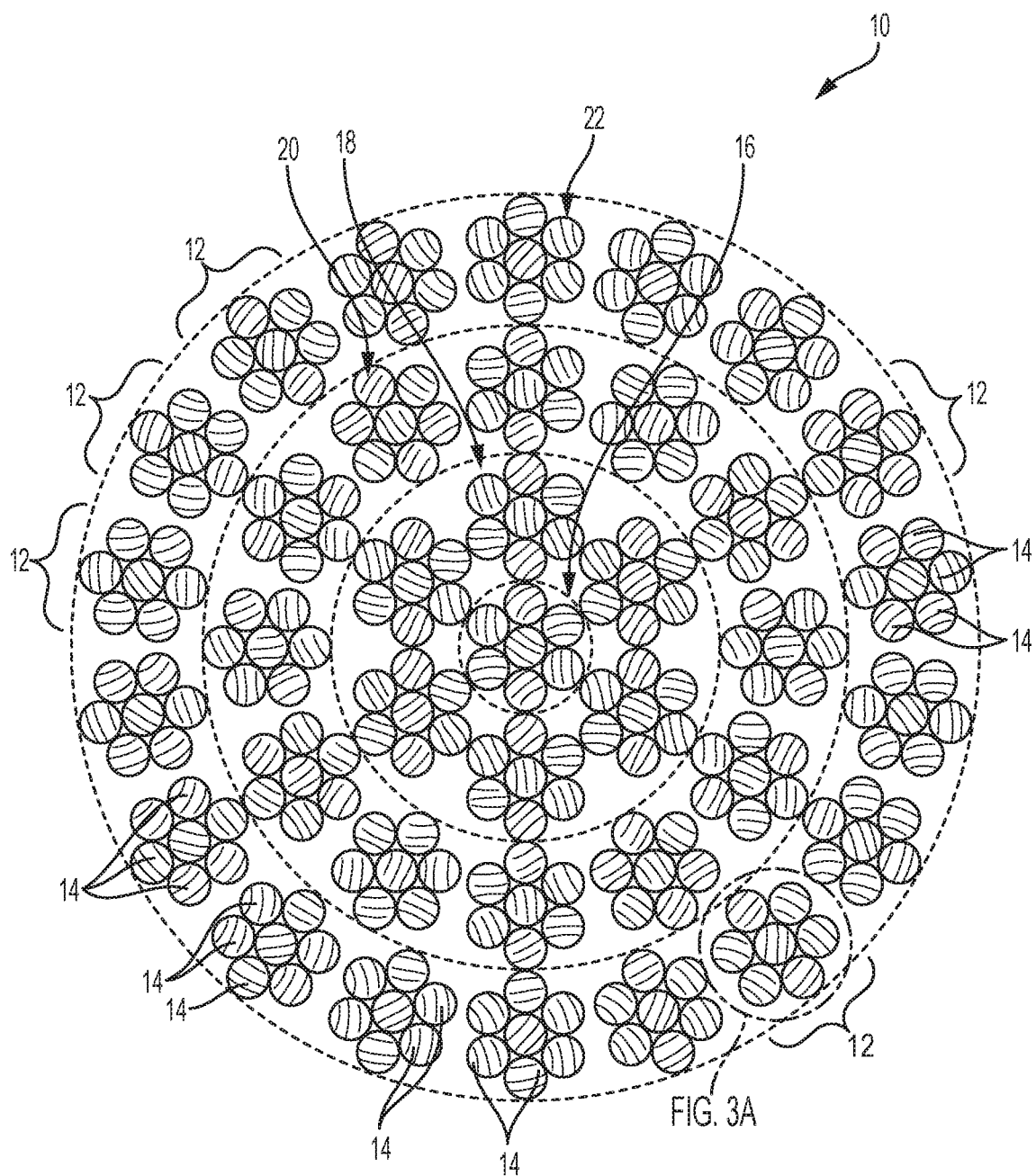
FIG. 1 is an end or sectional view of a cable in accordance with the present disclosure.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

Figure 2:
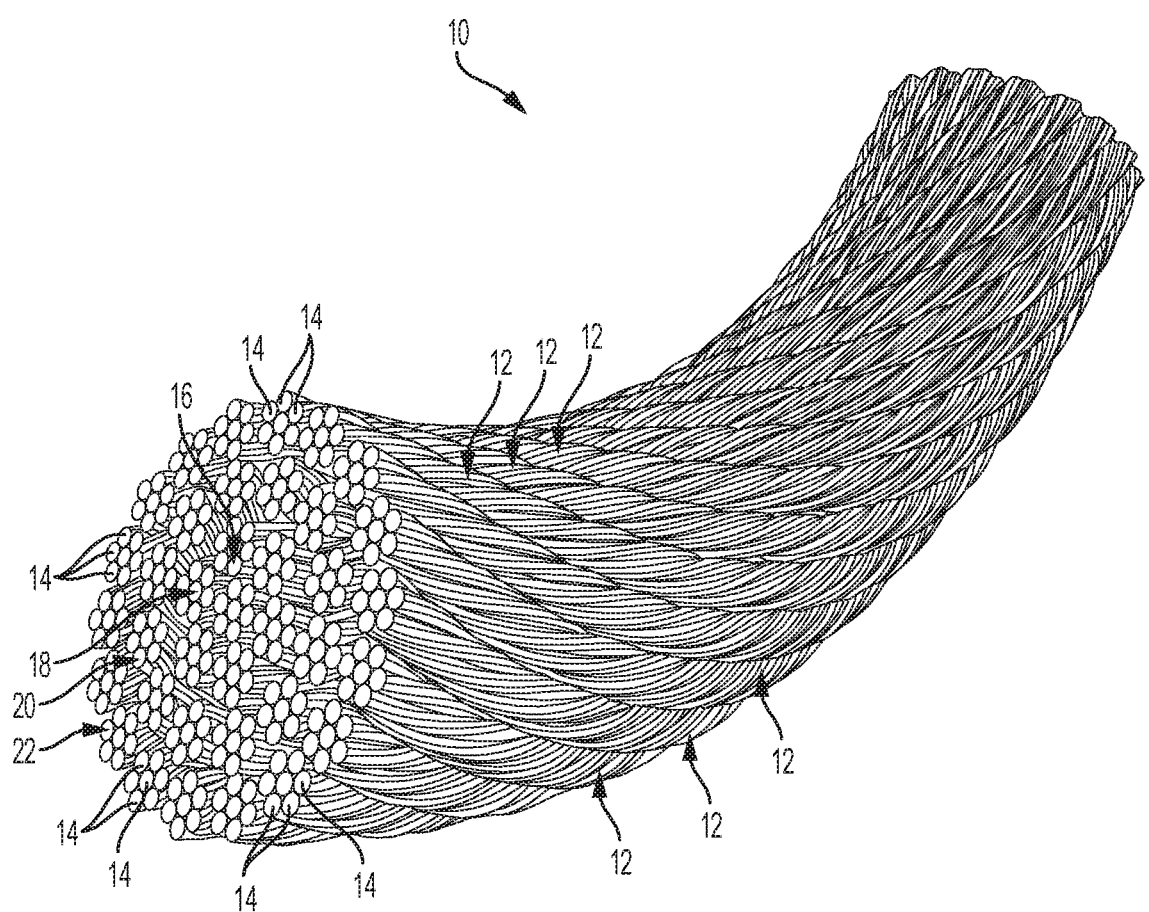
FIG. 2 is a perspective view of the cable of FIG. 1.

Referring to FIGS. 1 and 2, cable 10 is shown which, as described further below, is a small diameter, high strength, crush resistant, flexible cable including a plurality of strands 12 with each strand 12 including a plurality of individual wire filaments 14.

For purposes of the present disclosure, a cable construction is represented according to the nomenclature "[number of strands in the cable]×[number of wire filaments per strand]," where a wire filament (also known as a filar) is a single, monolithic drawn wire and a strand is a collection of wire filaments twisted or wound together. Cable 10 shown in FIGS. 1 and 2 is referred to as a "37×7" cable 10, meaning that cable 10 has thirty-seven strands 12, with each strand 12 including seven wire filaments 14.

In some designs, a central cable construct may be sheathed within another, outer cable construct. For purposes of the present disclosure, these designs are represented as "[number of strands in the central cable]×[number of wire filaments per strand in the central cable]+([number of strands in the outer cable]×[number of wire filaments per strand in the outer cable])". Thus, a "7×7+(8×19)" cable construct has a 7×7 construct forming a central cable, which is sheathed by eight strands each including 19 wire filaments forming an outer cable.

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In some exemplary embodiments, a wire or wire product in accordance with the present disclosure may have a diameter up to 2.5 mm.

"Impurities," "incidental impurities" and "trace impurities" and "unavoidable impurities" are material constituents present in a material at less than 500 parts per million or 0.05 wt. %.

1. Fine Wire Cable Construction

Wire filaments 14 of cable 10 may be drawn and wound wire filaments of high strength materials including, but not limited to, stainless steels, such as 302 (ASTM A313/A313M, ASTM A276, ASTM F899), 304V (ASTM F899, ASTM A276, ASTM A313/A313M), 304LV, 316LVM (ASTM A276, ASTM A580, ASTM F138, ISO 5832-1), and Custom 455 (ASTM A564/564M, ASTM F899), tungsten and molybdenum alloys, and cobalt chromium alloys such as L605 (ASTM F90, ISO 5832-5), 1058 (ASTM F1058, ISO 5832-7) 1537 (ASTM F1537, ISO 5832-12), MP35N (ASTM 562, ISO 5832-6), and 35N LT® (ASTM 562, ISO 5832-6) and nickel-titanium alloys. Each of the foregoing materials is available from Fort Wayne Metals Research Products Corp. of Fort Wayne, IN All of the ASTM standards mentioned above are hereby incorporated herein by reference, including their respective alloy constituency specifications. 35N LT® is further described in U.S. Pat. No. 8,048,369, assigned to the assignee of the present invention, the entire disclosure of which is incorporated by reference herein. A further exemplary material is Duplex 2205, as specified in the Unified Numbering System (UNS) as S32205, an in European Standards as EN144.62, these standards are incorporated herein by reference, including the alloy constituency of Duplex 2205 as specified therein.

Referring now to FIG. 1, the 37×7 cable 10 includes essentially four radial layers, including a first, central or core layer 16 having a single strand 12, a second layer 18 including six strands 12 which surround the first layer 16, a third layer 20 including twelve strands 12 which surround the second layer 18, and a fourth or outer layer 22 including eighteen strands 12 which surround the third layer 20. With the addition of each successive layer, a separate wire construct is formed within the larger construct of cable 10. For example, core layer 16 is a "1×7" wire construct because it is a single strand 12 of seven filaments 14. Second layer 18, when combined with core layer 16, can be considered a "7×7" wire construct because it has seven strands 12 each having seven filaments. In similar fashion, third layer 20 combines with layers 16 and 18 to form a "19×7" construct and outer layer 22 combines with layers 16, 18 and 20 to form a "37×7" construct.

Cable 10 is formed of strands 12 having fine-diameter, medical-grade filaments 14. As used herein, "medical-grade" materials are materials suitable for use within the human body, including the materials listed above. "Medical-grade" materials specifically exclude certain materials not suitable for use in, or in connection with medical procedures on, the human body. For examples non-medical grade materials are materials not suitable for contact with tissue and/or blood, including materials which cannot pass cytotoxicity testing of at least one hour of such contact. Non-medical grade materials include heavy metals including lead and cadmium, materials such as beryllium and beryllium copper, and any other materials generally regarded as toxic to the human body or otherwise damaging to human tissue. In the context of cable 10, other non-suitable materials may include carbon steels, brass, galvanized steels, tin, tin-plated materials, copper and copper alloys, aluminum, silver, nickel and nickel-based alloys (i.e., alloys having substantially more than 50% nickel), platinum, gold, and tantalum. Although some such materials may be considered "medical grade" in some contexts, they are low-strength and/or magnetic materials unsuitable for the high-strength medical device applications described herein. As such, the materials used to form filaments 14 are only medical-grade, low-magnetism or non-magnetic, and high-strength materials as described herein. Therefore, filaments 14 specifically exclude the foregoing non-medical grade, low-strength or magnetic materials beyond the level of unavoidable trace impurities.

In one embodiment, the overall outer diameter of cable 10 may be as little as 0.11 mm (0.0043 inches), 0.18 mm (0.0071 inches), 0.26 mm (0.0102 inches), 0.32 mm (0.0126 inches), or 0.43 mm (0.0169 inches), or may be as great as 1.0 mm (0.0394 inches), 2.0 mm (0.0787 inches), or 3.0 mm (0.118 inches), or may be within any range defined between any pair of the foregoing values. As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value. Thus, for example, any of the overall outer diameter ranges shown in Table 1 below may be employed for cable 10:

TABLE 1

Ranges of Overall Outer Cable Diameters 0.11 mm to 0.18 mm
0.11 mm to 0.26 mm
0.11 mm to 0.32 mm
0.11 mm to 0.43 mm
0.11 mm to 1.0 mm
0.11 mm to 2.0 mm
0.11 mm to 3.0 mm
0.18 mm to 0.26 mm
0.18 mm to 0.32 mm TABLE 1-continued Ranges of Overall Outer Cable Diameters 0.18 mm to 0.43 mm
0.18 mm to 1.0 mm
0.18 mm to 2.0 mm
0.18 mm to 3.0 mm
0.26 mm to 0.32 mm
0.26 mm to 0.43 mm
0.26 mm to 1.0 mm
0.26 mm to 2.0 mm
0.26 mm to 3.0 mm
0.32 mm to 0.43 mm
0.32 mm to 1.0 mm
0.32 mm to 2.0 mm
0.32 mm to 3.0 mm
0.43 mm to 1.0 mm
0.43 mm to 2.0 mm
0.43 mm to 3.0 mm
1.0 mm to 2.0 mm
1.0 mm to 3.0 mm
2.0 mm to 3.0 mm In the context of surgical instruments, particularly robotic instruments used in minimally invasive surgical procedures, the maximum diameter of 3 mm or less is the largest cable that would retain compatibility with such surgical devices. As noted herein, for example, such devices may have a maximum transverse dimension of 7-8 mm, such that any cables interacting with the device are commensurate in size. Despite these significant size constrains, the performance characteristics of the cable used in such a device, such as cable 10, are desirably maximized. In particular, cable 10 is capable of fitting within the very tight size constraints imposed by surgery instruments, while also minimizing bending stresses and providing adequate strength over a long service life.

The diameter of each strand 12 directly affects the overall diameter of cable 10, because exactly seven strands 12 span the overall diameter of cable 10 as shown in FIG. 1. Thus, to achieve the overall diameter ranges shown above, the diameter of filaments 14 in each strand 12 may be chosen based on the final desired diameter as well as other design factors, including material choice and the associated strength, ductility, and other mechanical or chemical properties of filaments 14. Thus, for cable 10 having a 37×7 configuration, the range of diameters for each strand 12 may be the same as the ranges specified in Table 1 for cable 10, but with each nominal value divided by about 7. In particular, the outer diameter of each strand 12 may be may be as little as 0.015 mm (0.0006 inches), 0.025 mm (0.0010 inches), 0.04 mm (0.0016 inches), 0.05 mm (0.0020 inches), or 0.06 mm (0.0024 inches), or may be as great as 0.14 mm (0.0055 inches), 0.29 mm (0.0114 inches), or 0.43 mm (0.0169 inches), or may be within any range defined between any pair of foregoing values. Thus, for example, any of the diameter ranges shown in Table 2 below may be employed for each individual strand 12 used in cable 10:

TABLE 2

Ranges of Outer Diameters for Individual Strands 0.015 mm to 0.025 mm
0.015 mm to 0.04 mm
0.015 mm to 0.05 mm
0.015 mm to 0.06 mm
0.015 mm to 0.14 mm
0.015 mm to 0.29 mm
0.015 mm to 0.43 mm
0.025 mm to 0.04 mm TABLE 2-continued Ranges of Outer Diameters for Individual Strands 0.025 mm to 0.05 mm
0.025 mm to 0.06 mm
0.025 mm to 0.14 mm
0.025 mm to 0.29 mm
0.025 mm to 0.43 mm
0.04 mm to 0.05 mm
0.04 mm to 0.06 mm
0.04 mm to 0.14 mm
0.04 mm to 0.29 mm
0.04 mm to 0.43 mm
0.05 mm to 0.06 mm
0.05 mm to 0.14 mm
0.05 mm to 0.29 mm
0.05 mm to 0.43 mm
0.06 mm to 0.14 mm
0.06 mm to 0.29 mm
0.06 mm to 0.43 mm
0.14 mm to 0.29 mm
0.14 mm to 0.43 mm
0.29 mm to 0.43 mm The strands 12 may be drawn or swaged prior to final layup of cable 10 (i.e., mating and winding of strands 12 together in the final construct), in order to mitigate potential peening damage between their wire elements and allow the stands 12 to move and settle with respect to one another.

Similarly, the diameter of each wire filament 14 directly affects the diameter of each strand 12, because exactly seven filaments 14 span the diameter of each strand 12 for a 37×7 cable construct, as shown in FIG. 1. Thus, for cable 10 having a 37×7 configuration, the range of diameters for each filament 14 may be the same as the ranges specified in Table 2 for cable 10, but with each nominal value divided by about 3. In particular, the diameters for filaments 14 may be as little as 0.005 mm (0.0002 inches), 0.007 mm (0.0003 inches), 0.009 mm (0.0004 inches), 0.012 mm (0.0005 inches), 0.015 mm (0.0006 inches), or 0.020 mm (0.0008 inches), or may be as great as 0.029 mm (0.0011 inches), 0.041 mm (0.0016 inches), 0.048 mm (0.0019 inches), 0.057 mm (0.0022 inches), 0.061 mm (0.0024 inches), 0.086 mm (0.0034 inches), 0.095 mm (0.0037 inches), or 0.143 mm (0.0056 inches), or may be within any range defined between any pair of foregoing values. Thus, for example, any of the diameter ranges shown in Table 3 below may be employed for each individual filament used in any of the strands 12 for cable 10:

TABLE 3

Ranges of Outer Diameters for Individual Filaments 0.005 mm to 0.007 mm
0.005 mm to 0.009 mm
0.005 mm to 0.012 mm
0.005 mm to 0.015 mm
0.005 mm to 0.020 mm
0.005 mm to 0.029 mm
0.005 mm to 0.041 mm
0.005 mm to 0.048 mm
0.005 mm to 0.057 mm
0.005 mm to 0.061 mm
0.005 mm to 0.086 mm
0.005 mm to 0.095 mm
0.005 mm to 0.143 mm
0.007 mm to 0.009 mm
0.007 mm to 0.012 mm
0.007 mm to 0.015 mm
0.007 mm to 0.020 mm
0.007 mm to 0.029 mm
0.007 mm to 0.041 mm TABLE 3-continued Ranges of Outer Diameters for Individual Filaments 0.007 mm to 0.048 mm
0.007 mm to 0.057 mm
0.007 mm to 0.061 mm
0.007 mm to 0.086 mm
0.007 mm to 0.095 mm
0.007 mm to 0.143 mm
0.009 mm to 0.012 mm
0.009 mm to 0.015 mm
0.009 mm to 0.020 mm
0.009 mm to 0.029 mm
0.009 mm to 0.041 mm
0.009 mm to 0.048 mm
0.009 mm to 0.057 mm
0.009 mm to 0.061 mm
0.009 mm to 0.086 mm
0.009 mm to 0.095 mm
0.009 mm to 0.143 mm
0.012 mm to 0.015 mm
0.012 mm to 0.020 mm
0.012 mm to 0.029 mm
0.012 mm to 0.041 mm
0.012 mm to 0.048 mm
0.012 mm to 0.057 mm
0.012 mm to 0.061 mm
0.012 mm to 0.086 mm
0.012 mm to 0.095 mm
0.012 mm to 0.143 mm
0.015 mm to 0.020 mm
0.015 mm to 0.029 mm
0.015 mm to 0.041 mm
0.015 mm to 0.048 mm
0.015 mm to 0.057 mm
0.015 mm to 0.061 mm
0.015 mm to 0.086 mm
0.015 mm to 0.095 mm
0.015 mm to 0.143 mm
0.020 mm to 0.029 mm
0.020 mm to 0.041 mm
0.020 mm to 0.048 mm
0.020 mm to 0.057 mm
0.020 mm to 0.061 mm
0.020 mm to 0.086 mm
0.020 mm to 0.095 mm
0.020 mm to 0.143 mm
0.029 mm to 0.041 mm
0.029 mm to 0.048 mm
0.029 mm to 0.057 mm
0.029 mm to 0.061 mm
0.029 mm to 0.086 mm
0.029 mm to 0.095 mm
0.029 mm to 0.143 mm
0.041 mm to 0.048 mm
0.041 mm to 0.057 mm
0.041 mm to 0.061 mm
0.041 mm to 0.086 mm
0.041 mm to 0.095 mm
0.041 mm to 0.143 mm
0.048 mm to 0.057 mm
0.048 mm to 0.061 mm
0.048 mm to 0.086 mm
0.048 mm to 0.095 mm
0.048 mm to 0.143 mm
0.057 mm to 0.061 mm
0.057 mm to 0.086 mm
0.057 mm to 0.095 mm
0.057 mm to 0.143 mm
0.061 mm to 0.086 mm
0.061 mm to 0.095 mm
0.061 mm to 0.143 mm
0.086 mm to 0.095 mm
0.086 mm to 0.143 mm
0.095 mm to 0.143 mm In cable 10, each wire filament 14 will typically have the same diameter, though such is not required as wire filaments 14 may have differing diameters either within or among individual strands 12. Thus, numerous combinations of filaments 14 may be utilized for a wide variety of diameters for strands 12 and overall diameters for cable 10. Moreover, any combination of the diameters from forty-nine filaments 14, each having any of the diameters listed above, may be combined to create an overall diameter of cable 10.

Further, although each wire filament 14 may be metallic in its form, some or all of the wire filaments 14 may be non-metallic and made of a polymer or glass material, for example.

Figure 3A:
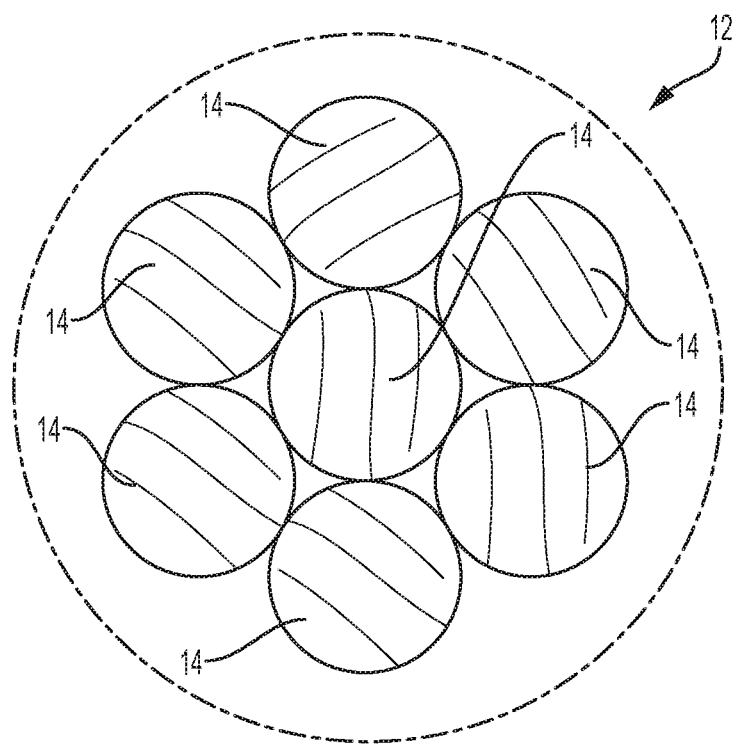
FIG. 3A is an enlarged view of a portion of FIG. 1, illustrating a 7-filament strand.
Figure 3B:
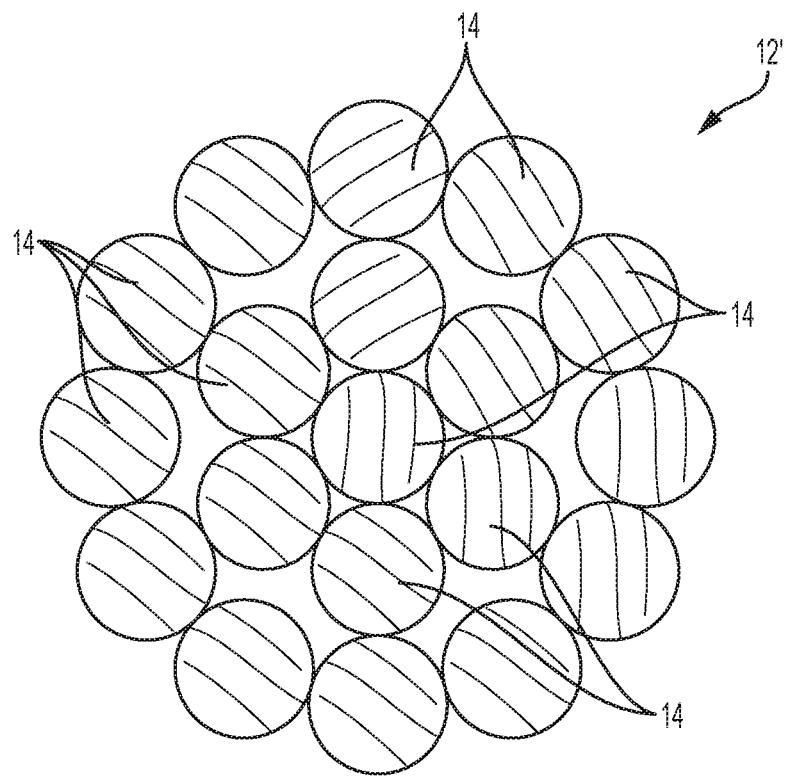
FIG. 3B is another enlarged view of a portion of FIG. 1, illustrating an alternative 19-filament strand.
Figure 3C:
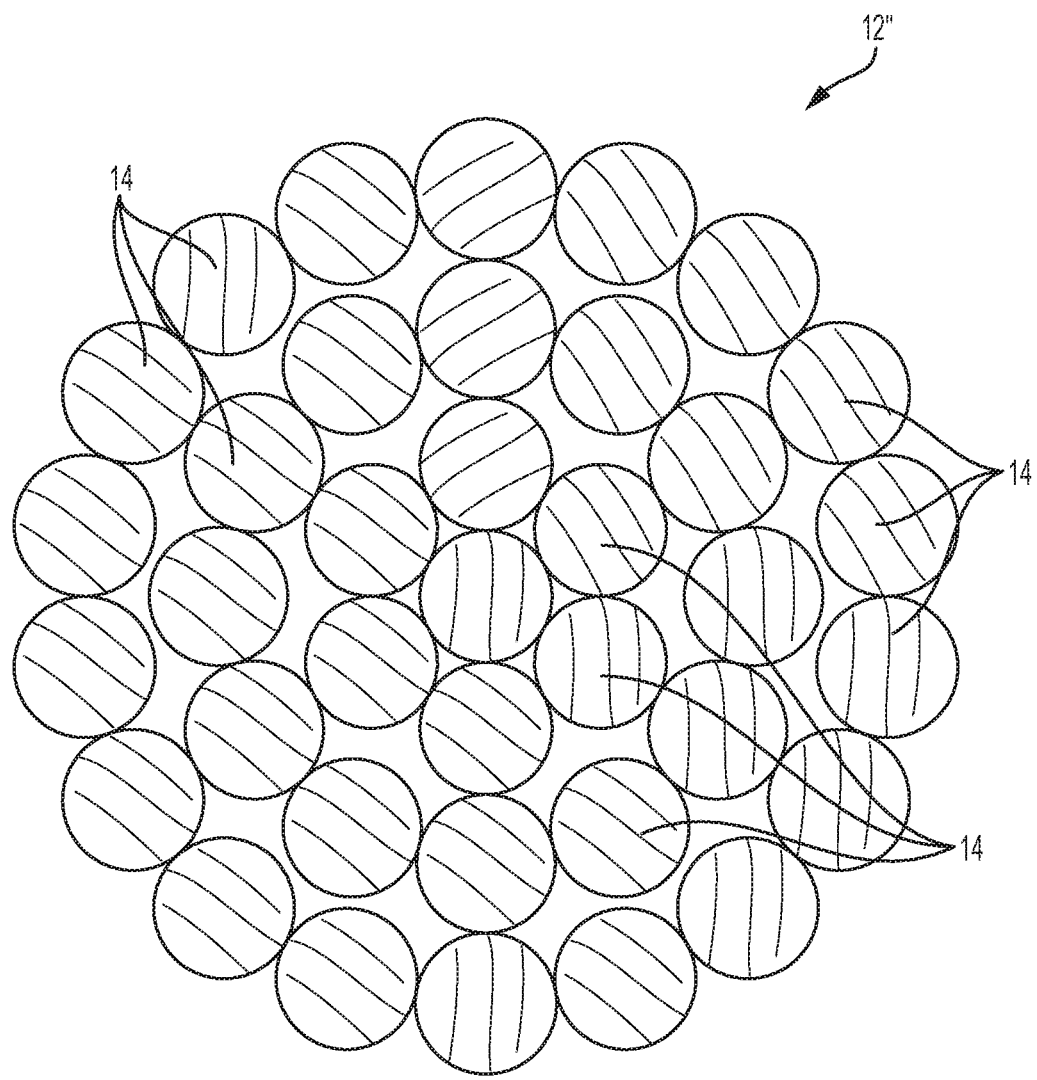
FIG. 3C is another enlarged view of a portion of FIG. 1, illustrating an alternative 37-filament strand.

In addition, the number of filaments in each strand 12, and the associated strand configuration, may also be modified and may affect the choice of diameter for filament 14. For example, the number of filaments per strand 12 may be greater than seven as shown in FIG. 3A. In one exemplary embodiment, one or more strands 12 of cable 10 may be replaced with strand 12' shown in FIG. 3B, which has nineteen individual filaments 14. In an embodiment where all strands 12 are replaced with strands 12', cable 10 may be classified as a "37×19" construct. In another exemplary embodiment, one or more strands 12 of cable 10 may be replaced with strand 12" shown in FIG. 3C, which has thirty-seven individual filaments 14. In an embodiment where all strands 12 are replaced with strands 12", cable 10 may be classified as a "37×37" construct.

The range of diameters for each individual filaments 14 in strands 12' and 12" is the same as the range of diameters for filaments 14 used in strand 12, except that the maximum diameters are reduced in order to remain within the designed overall diameter for cable 10 as detailed above. For filaments 14 used in the nineteen-filament strand 12', the maximum diameter of individual strands is 0.086 mm (0.0034 inches), yielding an overall construct diameter of 3.0 mm if all filaments 14 are of a common size. For filaments 14 used in the thirty-seven-filament strand 12", the maximum diameter of individual strands is 0.061 mm (0.0024 inches), also yielding an overall construct diameter of 3.0 mm if all filaments 14 are of a common size. For purposes of the present disclosure, "strand 12" can be taken to be interchangeable with strands 12' or 12", such that any discussion of "strand 12" can also be applied to strand 12' or 12".

Advantageously, in 37×19 and 37×37 constructs the additional numerousness of the filaments 14 as compared to the 37×7 construct described above may allow for the use of alloys having a nominally lower strength as compared to the relatively higher-strength alloys disclosed herein. In particular, the higher number of filaments 14 in the 37×19 and 37×37 constructs results in a relatively smaller diameter for individual filaments 14, for a given diameter of cable 10. This smaller filament diameter reduces the bending stresses of any given element. Although the net cross-sectional area of cable 10 also decreases as filament diameter decreases, the resulting reduction in tensile strength can be accounted for by material choice and overall cable diameter in many case, while the reduction in bending stresses can provide significant benefits in overall service life and capability in the context of medical device applications using cable and pulley arrangements or other tight-turn geometries for cable 10. In some embodiments, cables 10 employing strands 12' and/or strands 12" may be allowed to use stainless steel in place of tungsten used in strands 12, while still meeting a comparable bending stress and strength thresholds.

Lay length and lay factor, as well as the winding directions of the various strands 12 and filaments 14, are also variables which can be used to achieve superior performance for cable 10 in the context of fine-wire, small-diameter applications such as medical device pulley cables.

Figure 4:
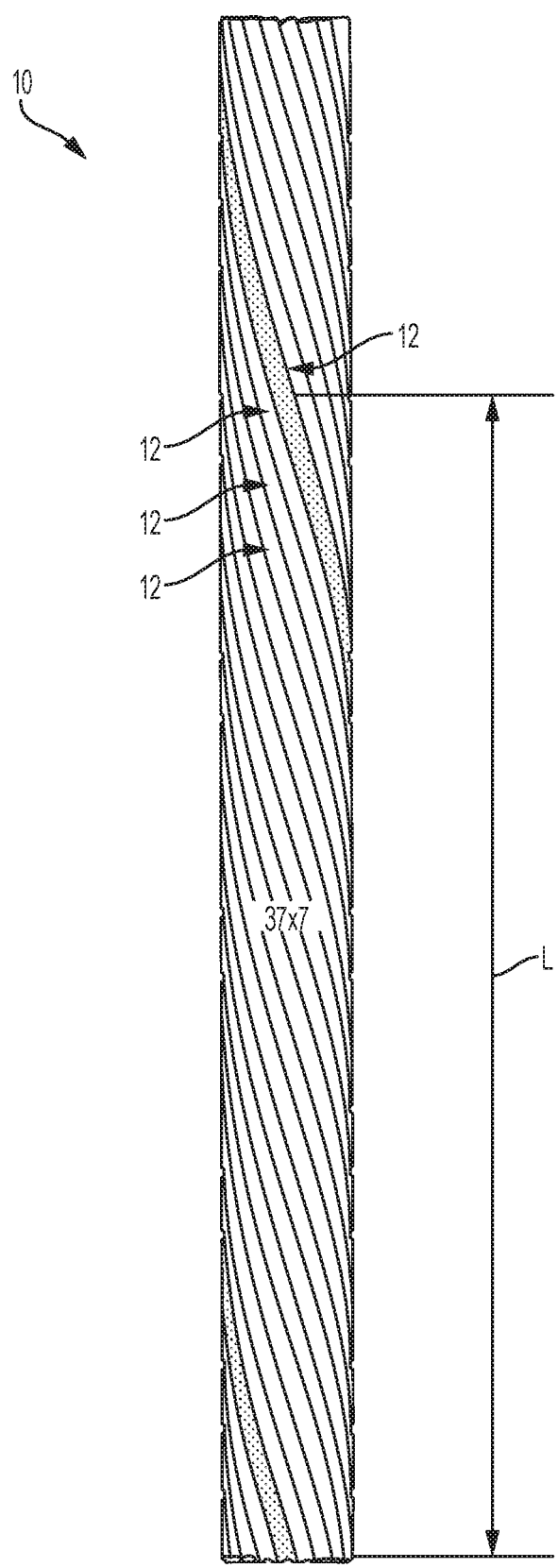
FIG. 4 is a plan view of the cable of FIG. 1.

As used herein, "lay length" or "pitch" means, for the wire filaments 14, the axial distance for one wire filament 14 to travel around the circumference of the strand 12 of which the wire filament 14 is a part. For strands 12, "lay length" or "pitch" means the axial distance for one strand 12 to travel around the circumference of the cable 10 of which the strand 12 is a part. Lay length L for strands 12 is illustrated, e.g., in FIG. 4.

As used herein, "lay factor" means the ratio of the lay length to the external diameter of the corresponding construct. Thus, when referring to the lay factor of filaments 14, the lay factor is the ratio of the lay length of filaments 14 to the diameter of the strand 12 of which that filament is a part. Similarly, the lay factor of a strand 12 is the ratio of the lay length of strand 12 to the overall diameter of cable 10. Unless otherwise specified herein, the "lay factor" of one of layers 16, 18, 20, 22 is the ratio of the lay length of the largest constituent to the diameter of the associated construct of which that constituent is a part. For example, the lay factor of core layer 16 is the ratio of the lay length of filaments 14 to the diameter of the strand 12 formed by such filaments 14. For outer layer 22, the lay factor is the ratio of the lay length of the outer strands 12 to the diameter of the overall cable 10 formed by such strands 12.

Lay length may be manipulated in a given design to affect axial strength and flexibility. In particular an increase in lay length can be employed to increase the axial strength for any given layer 16, 18, 20 and/or 22. On the other hand, lay length can be decreased to increase the flexibility for any given layer 16, 18, 20 and/or 22. Lay lengths (and therefore, lay factors) may be manipulated amongst the various layers 16, 18, 20 and 22 in order to provide the right mix of axial strength and flexibility for a given application.

For an exemplary embodiment of cable 10 usable in conjunction with a pulley 30 (FIG. 6) for a medical device, the lay factor throughout the layers 16, 18, 20, 22 of strands 12 may be as little as 5, 6, 7, 8 or 9 and as much as 11, 12, 13, 15 or 17, or may be within any range defined between any pair of foregoing values. Generally speaking, the lay factor for the core layer 16 will have a higher range (i.e., a higher shortest lay factor and a higher longest lay factor) than the corresponding ranges for the remaining layers 18, 20 and 22. In an exemplary embodiment of a 37×7 construct for cable 10, the respective layers of the construct may have varying lay factor ranges as follows:

First layer 16 may have a lay factor between 7 and 17, such as about 11.

Second layer 18 may have a lay factor between 5 and 13, such as about 7.

Third layer 20 may have a lay factor between 6 and 15, such as about 9.

Fourth layer 22 may have a lay factor between 6 and 15, such as about 9.

For a 37×19 cable construct substituting strands 12' (FIG. 3B) for strands 12 (FIG. 3A), first layer 16 may be considered to constitute two sub-layers 16A and 16B, with sub-layer 16A being a "1×7" construct and the combination of layers 16A and 16B being a "1×19" construct. Exemplary lay factors for the respective layers of the 37×19 configuration of cable 10 may have varying lay factor ranges as follows:

First sub-layer 16A may have a lay factor between 7 and 17, such as about 11.

First sub-layer 16B may have a lay factor between 7 and 15, such as about 9.

Second layer 18 may have a lay factor between 6 and 12, such as about 8.

Third layer 20 may have a lay factor between 6 and 15, such as about 9.

Fourth layer 22 may have a lay factor between 6 and 15, such as about 9.

For a 37×37 cable construct substituting strands 12" (FIG. 3C) for strands 12 (FIG. 3A), first layer 16 may be considered to constitute three sub-layers 16C, 16D and 16E, with sub-layer 16C being a "1×7" construct, the combination of layers 16C and 16D being a "1×19" construct, and the combination of layers 16C, 16D and 16E being a "1×37" construct. Exemplary lay factors for the respective layers of the 37×37 configuration of cable 10 may have varying lay factor ranges as follows:

First sub-layer 16A may have a lay factor between 7 and 17, such as about 11.

First sub-layer 16B may have a lay factor between 6 and 15, such as about 9.

First sub-layer 16C may have a lay factor between 6 and 15, such as about 9.

Second layer 18 may have a lay factor between 6 and 13, such as about 7.

Third layer 20 may have a lay factor between 6 and 15, such as about 9.

Fourth layer 22 may have a lay factor between 6 and 15, such as about 9.

For all the cable constructs listed above and described herein, the lay length may be computed by simply dividing the lay factor by the diameter of the relevant layer. The following Tables 4, 5 and 6 show the lay factors and lay lengths for the various layers in a 37×7 construct, a 37×19 construct, and a 37×37 construct respectively.

TABLE 4

Lay Factors and Lay Lengths for Exemplary 37 × 7 Cables

| Layer/Construction | Core/1 × 7 | 2nd/7 × 7 | 3rd/19 × 7 | Outer/ 37 × 7 |
|---|---|---|---|---|
| Cable Diameter: 0.11 mm | | | | |
| Nominal Diameter | 0.016 | 0.048 | 0.08 | 0.11 |
| Nominal Lay Factor | 11 | 7 | 9 | 9 |
| Nominal Lay Length | 0.178 | 0.33 | 0.711 | 0.991 |
| Short Lay Factor | 7 | 5 | 6 | 6 |
| Short Lay Length | 0.112 | 0.24 | 0.48 | 0.66 |
| Long Lay Factor | 17 | 13 | 15 | 15 |
| Long Lay Length | 0.272 | 0.624 | 1.2 | 1.65 |
| Cable Diameter: 0.32 mm | | | | |
| Nominal Diameter | 0.046 | 0.137 | 0.229 | 0.32 |
| Nominal Lay Factor | 11 | 7 | 9 | 9 |
| Nominal Lay Length | 0.508 | 0.965 | 2.057 | 2.87 |
| Short Lay Factor | 7 | 5 | 6 | 6 |
| Short Lay Length | 0.32 | 0.686 | 1.372 | 1.92 |
| Long Lay Factor | 17 | 13 | 15 | 15 |
| Long Lay Length | 0.777 | 1.783 | 3.429 | 4.8 |
| Cable Diameter: 0.43 mm | | | | |
| Nominal Diameter | 0.062 | 0.185 | 0.309 | 0.43 |
| Nominal Lay Factor | 11 | 7 | 9 | 9 |
| Nominal Lay Length | 0.686 | 1.295 | 2.769 | 3.861 |
| Short Lay Factor | 7 | 5 | 6 | 6 |
| Short Lay Length | 0.432 | 0.926 | 1.852 | 2.58 |
| Long Lay Factor | 17 | 13 | 15 | 15 |
| Long Lay Length | 1.049 | 2.407 | 4.629 | 6.45 |
| Cable Diameter: 3.0 mm | | | | |
| Nominal Diameter (mm) | 0.428 | 1.285 | 2.141 | 3 |
| Nominal Lay Factor | 11 | 7 | 9 | 9 |
| Nominal Lay Length (mm) | 4.699 | 8.992 | 19.279 | 27 |

TABLE 4-continued

Lay Factors and Lay Lengths for Exemplary 37 × 7 Cables

| Layer/Construction | Core/1 × 7 | 2nd/7 × 7 | 3rd/19 × 7 | Outer/37 × 7 |
|---|---|---|---|---|
| Short Lay Factor | 7 | 5 | 6 | 6 |
| Short Lay Length (mm) | 2.998 | 6.424 | 12.847 | 18 |
| Long Lay Factor | 17 | 13 | 15 | 15 |
| Long Lay Length (mm) | 7.28 | 16.702 | 32.118 | 45 |
| Cable Diameter: 2.0 mm | | | | |
| Nominal Diameter (mm) | 0.286 | 0.857 | 1.429 | 2 |
| Nominal Lay Factor | 11 | 7 | 9 | 9 |
| Nominal Lay Length (mm) | 3.15 | 5.994 | 12.852 | 18.009 |
| Short Lay Factor | 7 | 5 | 6 | 6 |
| Short Lay Length (mm) | 2 | 4.286 | 8.573 | 12 |
| Long Lay Factor | 17 | 13 | 15 | 15 |
| Long Lay Length (mm) | 4.858 | 11.144 | 21.431 | 30 |
| Cable Diameter: 1.0 mm | | | | |
| Nominal Diameter (mm) | 0.142 | 0.427 | 0.712 | 1 |
| Nominal Lay Factor | 11 | 7 | 9 | 9 |
| Nominal Lay Length (mm) | 1.575 | 2.997 | 6.401 | 8.992 |
| Short Lay Factor | 7 | 5 | 6 | 6 |
| Short Lay Length (mm) | 0.997 | 2.137 | 4.275 | 6 |
| Long Lay Factor | 17 | 13 | 15 | 15 |
| Long Lay Length (mm) | 2.422 | 5.557 | 10.687 | 15 |

TABLE 5

Lay Factors and Lay Lengths for Exemplary 37 × 19 Cables

Cable Diameter: 0.18 mm

| Layer/Construction | Core/1 × 7 | Core/1 × 19 | 2nd/7 × 19 | 3rd/19 × 19 | Outer/37 × 19 |
|---|---|---|---|---|---|
| Nominal Diameter (mm) | 0.015 | 0.025 | 0.076 | 0.127 | 0.18 |
| Nominal Lay Factor | 11 | 9 | 8 | 9 | 9 |
| Nominal Lay Length (mm) | 0.178 | 0.229 | 0.61 | 1.143 | 1.626 |
| Short Lay Factor | 7 | 7 | 6 | 6 | 6 |
| Short Lay Length (mm) | 0.107 | 0.178 | 0.457 | 0.762 | 1.08 |
| Long Lay Factor | 17 | 15 | 12 | 15 | 15 |
| Long Lay Length (mm) | 0.259 | 0.381 | 0.914 | 1.905 | 2.7 |

Cable Diameter: 0.32 mm

| Layer/Construction | 1 × 7 | 1 × 19 | 7 × 19 | 19 × 19 | 37 × 19 |
|---|---|---|---|---|---|
| Nominal Diameter (mm) | 0.027 | 0.046 | 0.137 | 0.229 | 0.32 |
| Nominal Lay Factor | 11 | 9 | 8 | 9 | 9 |
| Nominal Lay Length (mm) | 0.305 | 0.406 | 1.092 | 2.057 | 2.87 |
| Short Lay Factor | 7 | 7 | 6 | 6 | 6 |
| Short Lay Length (mm) | 0.192 | 0.32 | 0.823 | 1.372 | 1.92 |
| Long Lay Factor | 17 | 15 | 12 | 15 | 15 |
| Long Lay Length (mm) | 0.466 | 0.686 | 1.646 | 3.429 | 4.8 |

Cable Diameter: 0.43 mm

| Layer/Construction | 1 × 7 | 1 × 19 | 7 × 19 | 19 × 19 | 37 × 19 |
|---|---|---|---|---|---|
| Nominal Diameter (mm) | 0.037 | 0.061 | 0.183 | 0.305 | 0.43 |
| Nominal Lay Factor | 11 | 9 | 8 | 9 | 9 |
| Nominal Lay Length (mm) | 0.406 | 0.559 | 1.473 | 2.743 | 3.861 |
| Short Lay Factor | 7 | 7 | 6 | 6 | 6 |
| Short Lay Length (mm) | 0.256 | 0.427 | 1.097 | 1.829 | 2.58 |
| Long Lay Factor | 17 | 15 | 12 | 15 | 15 |
| Long Lay Length (mm) | 0.622 | 0.914 | 2.195 | 4.572 | 6.45 |

Cable Diameter: 3.0 mm

| Layer/Construction | 1 × 7 | 1 × 19 | 7 × 19 | 19 × 19 | 37 × 19 |
|---|---|---|---|---|---|
| Nominal Diameter (mm) | 0.257 | 0.428 | 1.284 | 2.14 | 3 |
| Nominal Lay Factor | 11 | 9 | 8 | 9 | 9 |
| Nominal Lay Length (mm) | 2.819 | 3.861 | 10.262 | 19.253 | 27 |
| Short Lay Factor | 7 | 7 | 6 | 6 | 6 |
| Short Lay Length (mm) | 1.798 | 2.996 | 7.704 | 12.84 | 18 |
| Long Lay Factor | 17 | 15 | 12 | 15 | 15 |
| Long Lay Length (mm) | 4.365 | 6.42 | 15.408 | 32.099 | 45 |

Cable Diameter: 2.0 mm

| Layer/Construction | 1 × 7 | 1 × 19 | 7 × 19 | 19 × 19 | 37 × 19 |
|---|---|---|---|---|---|
| Nominal Diameter (mm) | 0.171 | 0.286 | 0.857 | 1.429 | 2 |
| Nominal Lay Factor | 11 | 9 | 8 | 9 | 9 |

TABLE 5-continued

Lay Factors and Lay Lengths for Exemplary 37 × 19 Cables

| | | | | | |
|---|---|---|---|---|---|
| Nominal Lay Length (mm) | 1.88 | 2.565 | 6.858 | 12.852 | 18.009 |
| Short Lay Factor | 7 | 7 | 6 | 6 | 6 |
| Short Lay Length (mm) | 1.2 | 2 | 5.144 | 8.573 | 12 |
| Long Lay Factor | 17 | 15 | 12 | 15 | 15 |
| Long Lay Length (mm) | 2.915 | 4.286 | 10.287 | 21.431 | 30 |

Cable Diameter: 1.0 mm

| Layer/Construction | 1 × 7 | 1 × 19 | 7 × 19 | 19 × 19 | 37 × 19 |
|---|---|---|---|---|---|
| Nominal Diameter (mm) | 0.085 | 0.142 | 0.427 | 0.711 | 1 |
| Nominal Lay Factor | 11 | 9 | 8 | 9 | 9 |
| Nominal Lay Length (mm) | 0.94 | 1.27 | 3.404 | 6.401 | 8.992 |
| Short Lay Factor | 7 | 7 | 6 | 6 | 6 |
| Short Lay Length (mm) | 0.597 | 0.996 | 2.56 | 4.267 | 6 |
| Long Lay Factor | 17 | 15 | 12 | 15 | 15 |
| Long Lay Length (mm) | 1.451 | 2.134 | 5.121 | 10.668 | 15 |

TABLE 6

Lay Factors and Lay Lengths for Exemplary 37 × 37 Cables

Cable Diameter: 0.26 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.016 | 0.027 | 0.037 | 0.112 | 0.187 | 0.26 |
| Nominal Lay Factor | 11 | 9 | 9 | 7 | 9 | 9 |
| Nominal Lay Length (mm) | 0.178 | 0.229 | 0.33 | 0.787 | 1.676 | 2.337 |
| Short Lay Factor | 7 | 6 | 6 | 6 | 6 | 6 |
| Short Lay Length (mm) | 0.112 | 0.16 | 0.224 | 0.672 | 1.12 | 1.56 |
| Long Lay Factor | 17 | 15 | 15 | 13 | 15 | 15 |
| Long Lay Length (mm) | 0.272 | 0.4 | 0.56 | 1.456 | 2.8 | 3.9 |

Cable Diameter: 0.32 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.02 | 0.033 | 0.046 | 0.139 | 0.231 | 0.32 |
| Nominal Lay Factor | 11 | 9 | 9 | 7 | 9 | 9 |
| Nominal Lay Length (mm) | 0.229 | 0.305 | 0.406 | 0.965 | 2.083 | 2.87 |
| Short Lay Factor | 7 | 6 | 6 | 6 | 6 | 6 |
| Short Lay Length (mm) | 0.139 | 0.198 | 0.277 | 0.832 | 1.387 | 1.92 |
| Long Lay Factor | 17 | 15 | 15 | 13 | 15 | 15 |
| Long Lay Length (mm) | 0.337 | 0.495 | 0.693 | 1.803 | 3.467 | 4.8 |

Cable Diameter: 0.43 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.027 | 0.044 | 0.062 | 0.187 | 0.311 | 0.43 |
| Nominal Lay Factor | 11 | 9 | 9 | 7 | 9 | 9 |
| Nominal Lay Length (mm) | 0.305 | 0.406 | 0.559 | 1.295 | 2.794 | 3.861 |
| Short Lay Factor | 7 | 6 | 6 | 6 | 6 | 6 |

TABLE 6-continued

Lay Factors and Lay Lengths for Exemplary 37 x 37 Cables

| | | | | | | |
|---|---|---|---|---|---|---|
| Short Lay Length (mm) | 0.187 | 0.267 | 0.373 | 1.12 | 1.867 | 2.58 |
| Long Lay Factor | 17 | 15 | 15 | 13 | 15 | 15 |
| Long Lay Length (mm) | 0.453 | 0.667 | 0.933 | 2.427 | 4.667 | 6.45 |

Cable Diameter: 3.0 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.184 | 0.306 | 0.428 | 1.285 | 2.142 | 3 |
| Nominal Lay Factor | 11 | 9 | 9 | 7 | 9 | 9 |
| Nominal Lay Length (mm) | 2.032 | 2.743 | 3.861 | 8.992 | 19.279 | 27 |
| Short Lay Factor | 7 | 6 | 6 | 6 | 6 | 6 |
| Short Lay Length (mm) | 1.285 | 1.836 | 2.571 | 7.713 | 12.855 | 18 |
| Long Lay Factor | 17 | 15 | 15 | 13 | 15 | 15 |
| Long Lay Length (mm) | 3.122 | 4.591 | 6.427 | 16.711 | 32.137 | 45 |

Cable Diameter: 2.0 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.123 | 0.204 | 0.286 | 0.859 | 1.431 | 2 |
| Nominal Lay Factor | 11 | 9 | 9 | 7 | 9 | 9 |
| Nominal Lay Length (mm) | 1.346 | 1.829 | 2.565 | 6.02 | 12.878 | 18.009 |
| Short Lay Factor | 7 | 6 | 6 | 6 | 6 | 6 |
| Short Lay Length (mm) | 0.859 | 1.227 | 1.718 | 5.153 | 8.588 | 12 |
| Long Lay Factor | 17 | 15 | 15 | 13 | 15 | 15 |
| Long Lay Length (mm) | 2.086 | 3.067 | 4.294 | 11.164 | 21.469 | 30 |

Cable Diameter: 1.0 mm

| Layer / Construction | Core / 1 × 7 | Core / 1 × 19 | Core / 1 × 37 | 2nd / 7 × 37 | 3rd / 19 × 37 | Outer / 37 × 37 |
|---|---|---|---|---|---|---|
| Nominal Diameter (mm) | 0.061 | 0.102 | 0.142 | 0.427 | 0.711 | 1 |
| Nominal Lay Factor | 11 | 9 | 9 | 7 | 9 | 9 |
| Nominal Lay Length (mm) | 0.66 | 0.914 | 1.27 | 2.997 | 6.401 | 8.992 |
| Short Lay Factor | 7 | 6 | 6 | 6 | 6 | 6 |
| Short Lay Length (mm) | 0.427 | 0.61 | 0.853 | 2.56 | 4.267 | 6 |
| Long Lay Factor | 17 | 15 | 15 | 13 | 15 | 15 |
| Long Lay Length (mm) | 1.036 | 1.524 | 2.134 | 5.547 | 10.668 | 15 |

The strands 12 of the second, third, and fourth layers 18, 20 and 22 may be wound in alternating, sequentially opposite helical directions. For example, the strands 12 of second layer 18 may be wound in a first helical direction, the strands 12 of third layer 20 in a second, opposite helical direction, and the strands 12 of fourth layer 22 in the same helical direction as strands 12 of second layer 18. This arrangement is illustrated in, e.g., FIG. 2.

Advantageously, with the strands 12 of adjacent layers wound in opposite helical directions, when cable 10 is subjected to axial/tensile loading to generate an unwinding force, because the layers are wound in opposite helical directions the unwinding forces of the layers tend to act opposite one another and thereby maintain the winding integrity of the cable layers. In this manner, the overall cable 10 has a high tensile stability and resistance to unwinding and may be referred to as a "non-rotating" cable. Thus, cable 10 provides a high axial and torsional load carrying capability without inducing torque or "spin" within cable 10 itself or within the device in which cable 10 is incorporated.

Further, cable 10 may be assembled in a "regular lay" construction, in which the wire filaments 14 of each strand 12 are wound in a first helical direction, with the strands 12 themselves wound in a second, opposite helical direction. The foregoing discussion of cable 10 assumes a "regular lay" construction. Alternatively, cable 10 may be made in a "Lang's lay" construction, in which filaments 14 of each strand 12 are wound in a first helical direction, with the strands 12 themselves wound in the same first helical direction. In the case of a Lang's lay configuration, adjacent layers 16, 18, 20, 22 may be wound in the same helical direction, rather than an opposite helical direction as described above.

The final cable 10 may itself be swaged, drawn, heat treated (annealed), and/or coated or over-braided as desired.

2. Medical Device Applications

Cable 10 will be further described below with reference to an exemplary medical device application in which cable 10 may be used, such as an endoscope device which includes a relatively small diameter pulley 30, shown in FIG. 5. Pulley 30 defines a root diameter, shown as dimension RD in FIG. 5, which may be as little as 1 mm, 2 mm, or 3 mm or as great as 4 mm, 5 mm or 6 mm, for example. Referring to FIG. 6, when disposed around pulley 30, due to the small diameter of pulley 30, cable 10 will need to accommodate a very high amount of bending strain for cable 10 to remain properly seated within the pulley space 32 defined within the root diameter RD of pulley 30 while cable 10 is subjected to tensile loading.

In this connection, one typical problem with existing cables is that the individual wire filaments of the cables are too large in diameter to accommodate the bending stresses imposed by such small pulleys. In addition, because the cables are subjected to relatively high tensile loads, the use of relatively larger diameter wire filaments minimizes the contact points or total contact area, between the outermost periphery of the cable with the pulley, thereby leading to potential disengagement of the cable from the pulley.

In many industrial, large-scale applications, pulleys will typically have a root diameter which is much larger than the diameter of an associated cable, such as 15, 20, 25, or 40 times the diameter of the cable. However, in the present medical device application, the root diameter RD of pulley 30 may be between 3 and 6 times the outer diameter of cable 10, such as 3, 4, 5, or 6 times the diameter of cable 10.

Advantageously, cable 10 provides good resistance to bending stress in that the outer diameter of the individual wire filaments 14 is minimized such that the wire filament count, or "filar" count, of cable 10 is high to provide reduced bending strain. As may be seen in FIG. 6 and as described further in the Example below, the minimized outer diameter of the wire filaments 14 of cable 10, as well as the relatively small number of wire filaments 14 in each strand 12 with the number of strands 12 being high in the outermost layer 22 of cable 10, the outmost periphery of cable 10 closely approximates a cylinder, such that cable 10 will maintain substantial area contact with the adjacent (generally cylindrical) surface of pulley 30.

Figure 5:
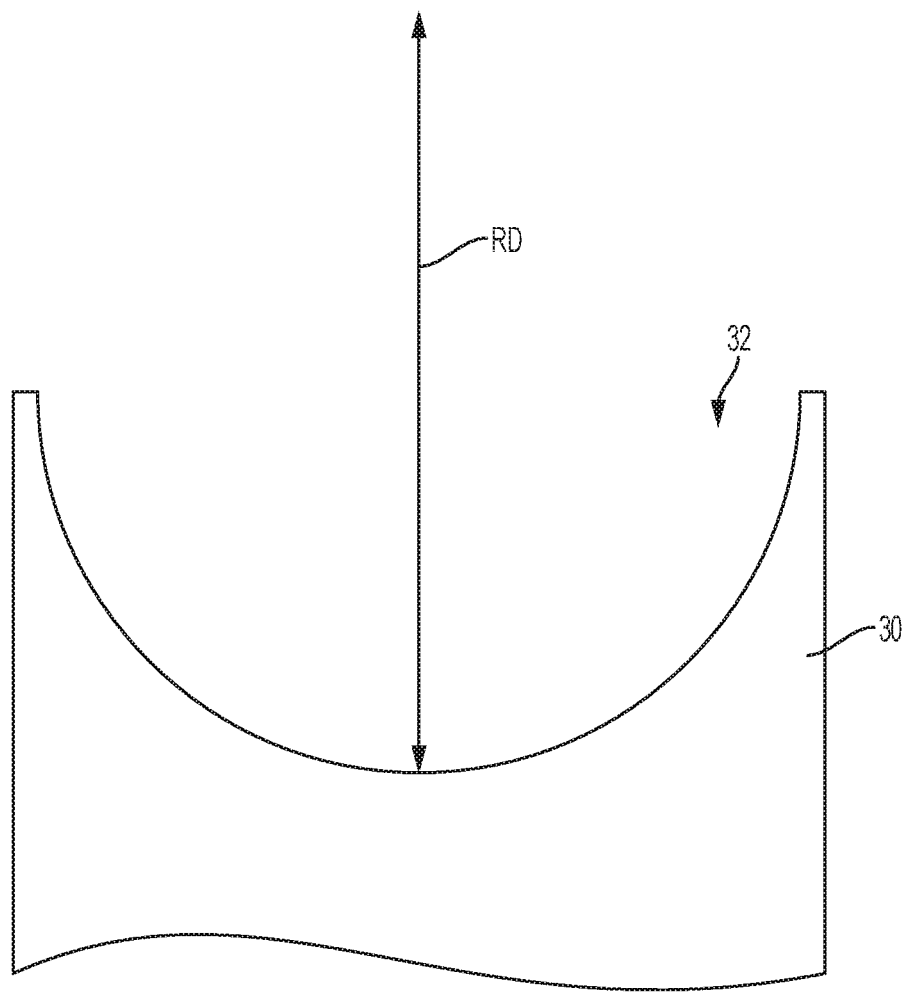
FIG. 5 is a partial sectional view of a pulley.
Figure 6:
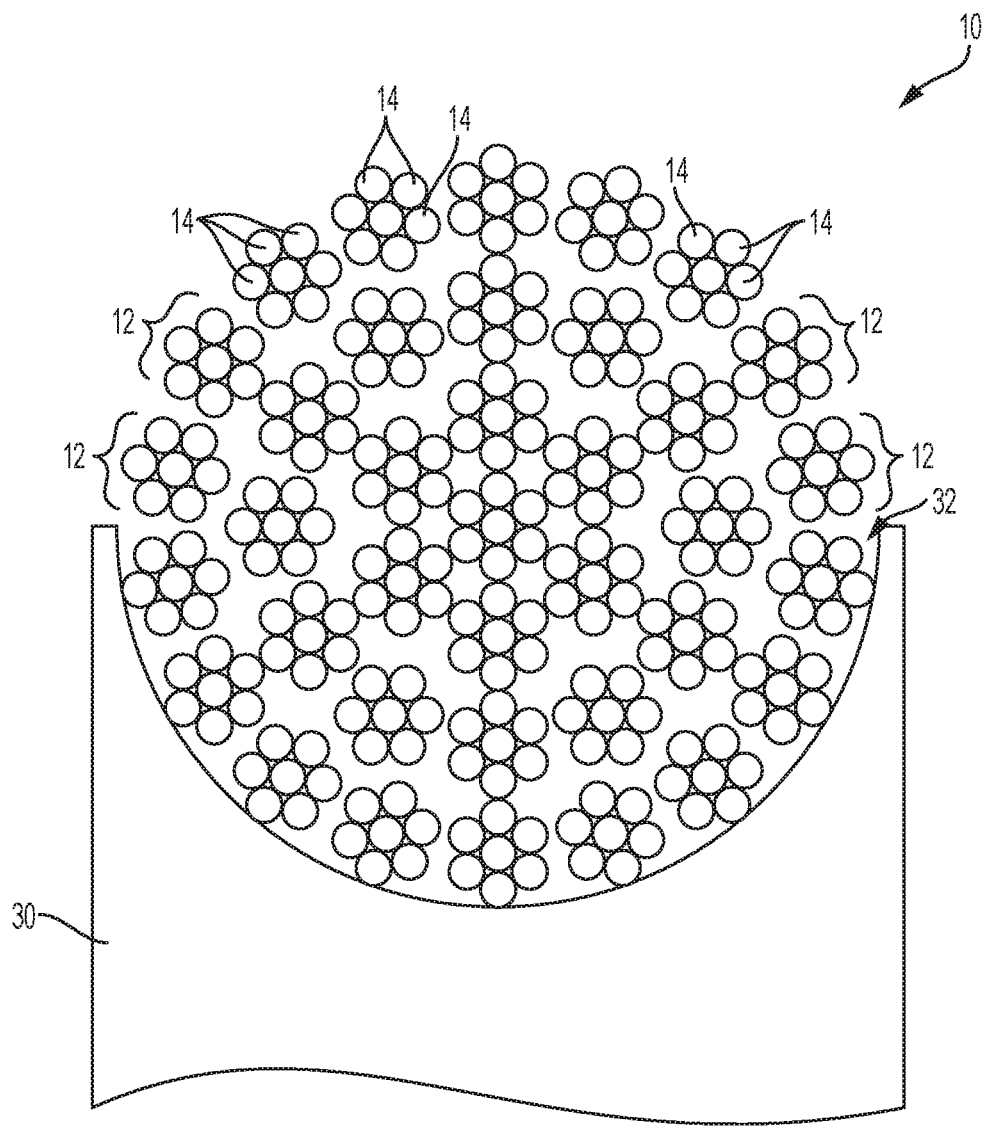
FIG. 6 is a view of the pulley of FIG. 5, carrying the cable of FIGS. 1 and 2.

Cable 10 further exhibits resistance to crushing or flattening when used in a system of pulleys or sheaves or other guiding surfaces of the type shown in FIG. 5, such as pulley surfaces of small diameter as in surgical instruments or robotic systems. In particular, cable 10 has a greater surface area in contact with the pulley 30 therefore distributing normal forces and resulting in lower contact stress.

In the above manner, in the field of medical devices such as endoscopes, cable 10 provides increased design flexibility due to its superior bending stress characteristics for a given tensile load rating. Similarly, cable 10 provides a high-performance, long-lasting replacement for cables used in existing medical device designs.

Potential applications of cable 10 include continuum robots/endoscopes, "snake-like" robots/endoscopes, high precision linear/cable extensometers, nitinol actuators (which benefit from low torsion when loaded/actuated), safety lock wires (which benefit from not untwisting when tensioned), cerclage systems, catheter and delivery systems (which maintain planarity when deflected), electrophysiology catheters, prosthetics (which benefit from quiet running due to smooth surface in conduits), cutting of extruded foods, industrial catalysts, stabilizing arms, endoscopy, robotic surgery, aerospace tension members (spacecraft), antennae arrays, mechanical drive systems, cable extension position sensors, and mechatronic applications.

EXAMPLE

In this Example, it is demonstrated that a 37×7 wire cable in accordance with the present disclosure contacts a mating sheave or pulley with approximately 61% greater contact area as compared to an equally sized 8×19 construction, and with approximately 164% greater contact area than a 7×37 construction.

A typical robotic end effector cable includes 201 wire filaments arranged in an 8×19 construction ("8×19"). Using 0.021 inch diameter as a baseline the pulley contacts points of a 37×7 wire rope are calculated vs. the 8×19 and 7×37 configurations of the same diameter.

TABLE 7

Comparison of Exemplary Cables with Experimental Control Cables

| Construction | Filar Diameter Multiple | Strand Element Dia (mm) | Cable Dia (mm) | Lay Diameter (mm) | Strand Length (mm) | Strand Elements per Lay (qty) | Contacts (per unit length) (qty) |
| --- | --- | --- | --- | --- | --- | --- | --- |
| 37 × 7 | 21 | 0.025 | 0.08 | 0.53 | 4.80 | 18 | 95 |
| 37 × 19 | 35 | 0.015 | | 0.53 | 4.80 | 18 | 95 |
| 37 × 37 | 49 | 0.011 | | 0.53 | 4.80 | 18 | 95 |

TABLE 7-continued

Comparison of Exemplary Cables with Experimental Control Cables

| Construction | Diameter Multiple | Filar Dia (mm) | Strand Element Dia (mm) | Cable Diameter (mm) | Lay Length (mm) | Strand Elements per Lay (qty) | Contacts (per unit length) (qty) |
|---|---|---|---|---|---|---|---|
| 7 × 7 + 8(1 × 19) | 19 | 0.028 | 0.14 | 0.53 | 3.47 | 8 | 59 |
| 7 × 37 | 21 | 0.025 | 0.13 | 0.53 | 4.27 | 6 | 36 |

Figure 7:
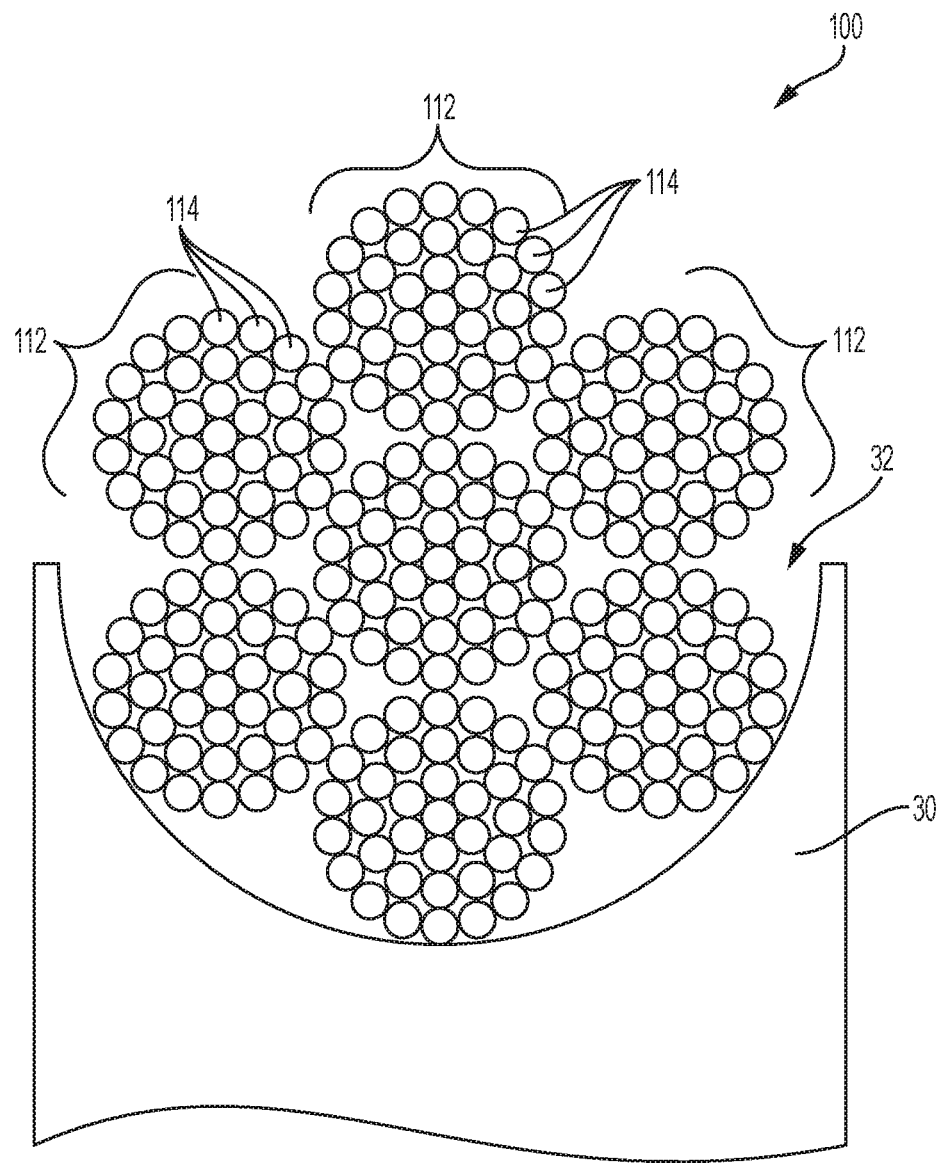
FIG. 7 is a view of the pulley of FIG. 5, carrying a 7×37 cable.
Figure 8:
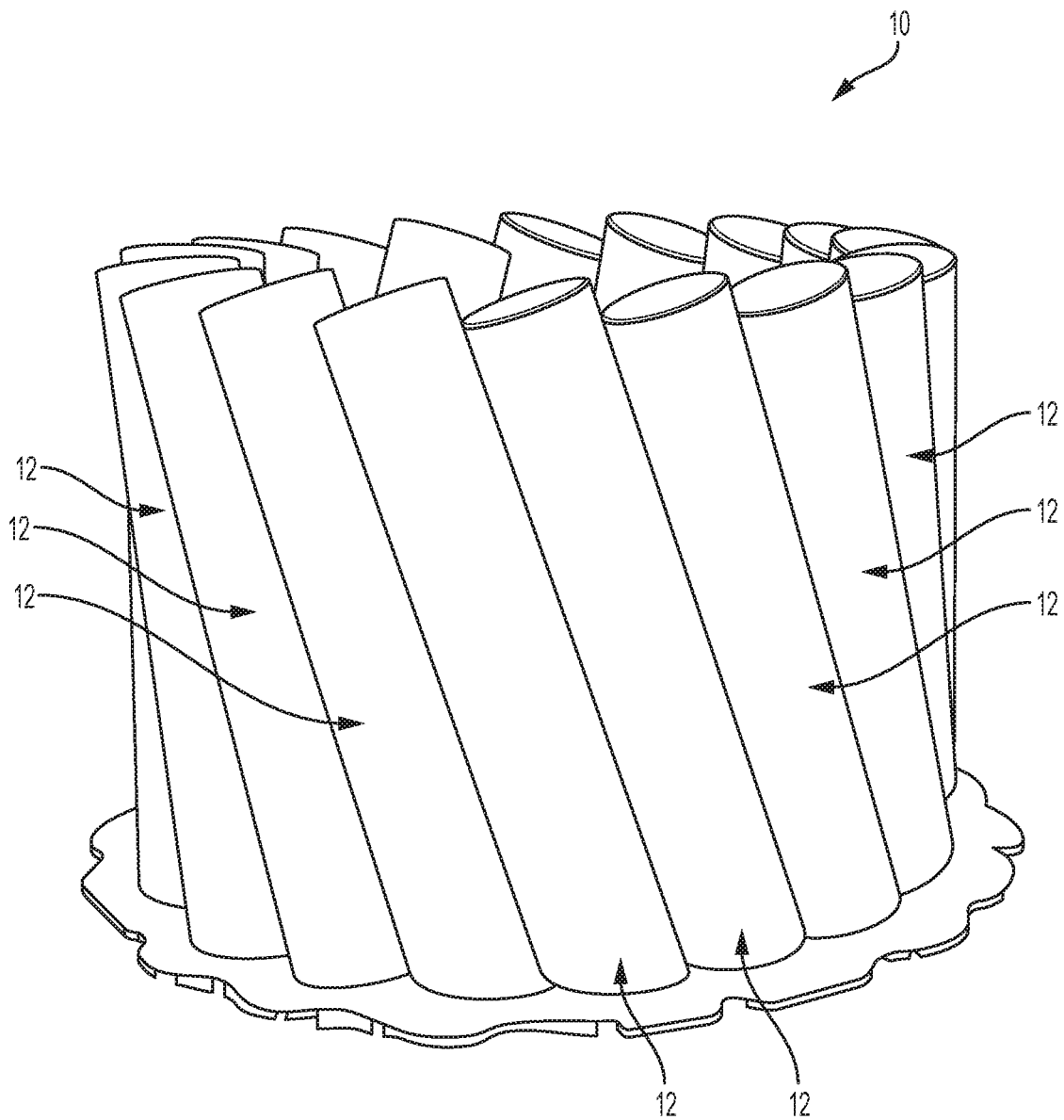
FIG. 8 corresponds to Example 1, and is a sectioned rendering of a 37×7 cable.
Figure 9:
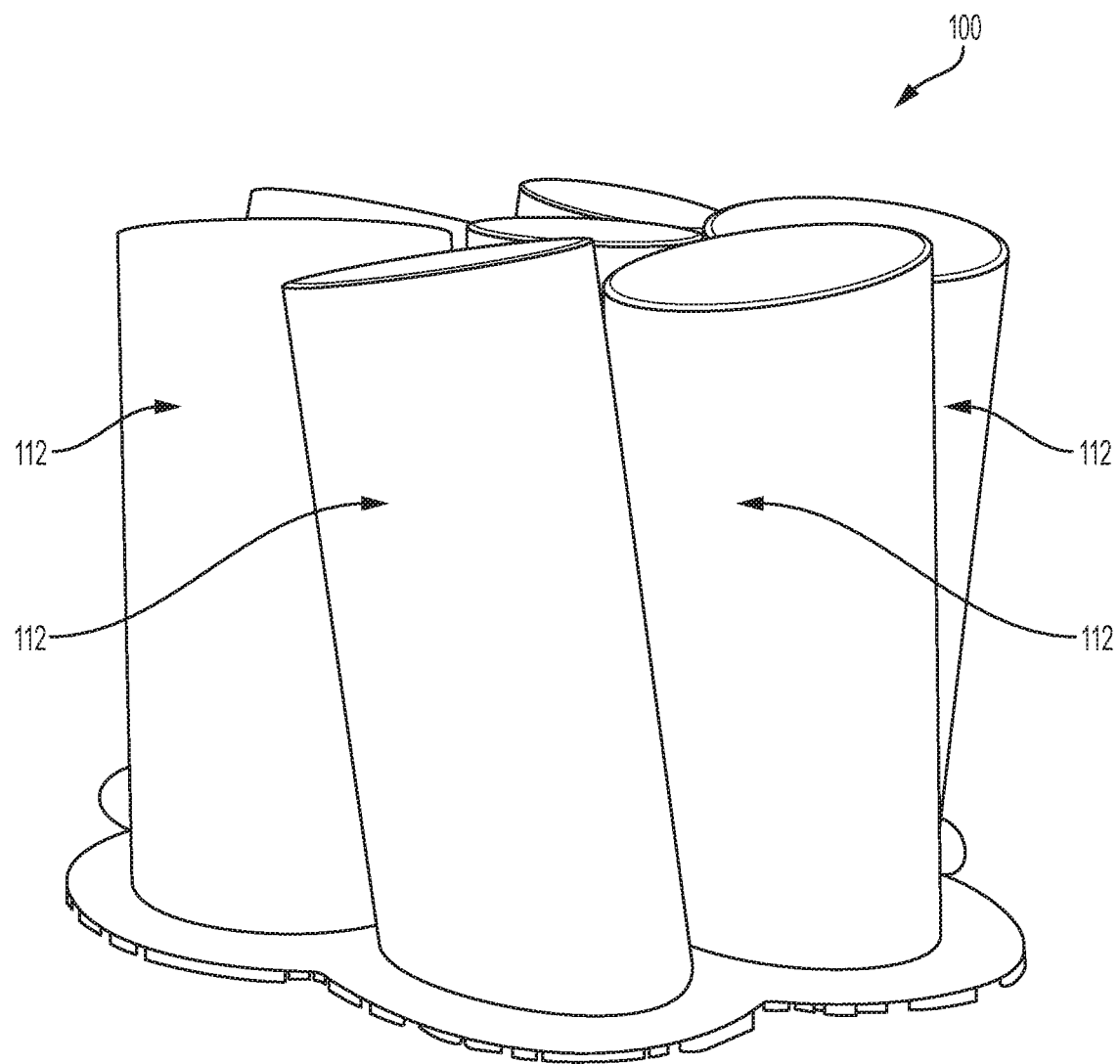
FIG. 9 also corresponds to Example 1, and is a sectioned rendering of a 7×37 cable.

Improvement in Pulley Contact Points compared to 7 × 7 + 8(1 × 19): $\frac{95-59}{59} * 100 = 61\%$ Improvement in Pulley Contact Points compared to 7 × 37: $\frac{95-36}{36} * 100 = 164\%$ The 37×7 configuration is shown in cross section as cable 10 in FIG. 6, while a 7×37 configuration is shown as cable 100 in cross section in FIG. 7. The outer strand elements 12 of the 37×7 configuration vs. the outer strand elements 112 of the 7×37 configuration are schematically shown in FIGS. 8 and 9, respectively, to highlight the exterior layer surfaces of each configuration that are available for contacting a pulley or sheave. As shown in FIG. 7 and exemplified in Table 7 above, the much larger outer layer of strands 112 formed of filaments 114 in the 7×37 construct will leave substantial portions of the cable unsupported by an adjacent surface of the pulley or sheave 30. By contrast, as shown in FIG. 6, the much smaller outer layer of strands 12 formed of filaments 14 in the 37×7 configuration more closely approximate a cylinder, such that the cable 10 will maintain substantial contact with an adjacent (generally cylindrical) surface of a pulley or sheave. This results in a 61% increase in the number of pulley contact points of a 37×7 construct as compared to a 7×7+8(1×19) construct, and a 164% increase as compared to a 7×37 construct.

37×19 and 37×37 constructions using strands 12' (FIG. 3B) or strands 12" (FIG. 3C) show similar improvements in pulley contact.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A wire cable comprising:
   37 strands, each strand including at least 7 wire filaments, each of the wire filaments formed from a medical-grade material, the strands arranged in layers comprising:
   a first, central layer of a single strand;
   a second layer of six strands;
   a third layer of twelve strands; and
   a fourth, outermost layer of eighteen strands,
   the wire filaments each having a diameter between 0.005 mm and 0.143 mm, and the wire cable having an outermost diameter between 0.11 mm and 3.0 mm; and
   wherein a lay factor of each of the first through fourth layers is between 5 and 17.

2. The wire cable of claim 1, wherein the wire filaments are made of a metallic material selected from the group consisting of stainless steel, tungsten, and cobalt chromium alloys.

3. The wire cable of claim 2, wherein the wire filaments are all made from the same metallic material.

4. The wire cable of claim 3, wherein the wire filaments are all formed with a common diameter.

5. The wire cable of claim 1, wherein each strand includes 19 of the wire filaments.

6. The wire cable of claim 5, wherein the diameters of the wire filaments are between 0.005 mm and 0.086 mm.

7. The wire cable of claim 1, wherein each strand includes 37 of the wire filaments.

8. The wire cable of claim 7, wherein the diameters of the wire filaments are between 0.005 mm and 0.061 mm.

9. The wire cable of claim 1, wherein:
   the lay factor of the first layer is between 7 and 17;
   the lay factor of the second layer is between 5 and 13;
   the lay factor of the third layer is between 6 and 15; and
   the lay factor of the fourth layer is between 6 and 15.

10. The wire cable of claim 1, wherein each of the wire filaments comprise tungsten.

11. The wire cable of claim 1, wherein each of the wire filaments comprise stainless steel.

12. A wire cable comprising:
   37 strands, each strand including at least 7 wire filaments, each of the wire filaments formed from a medical-grade material, the strands arranged in layers comprising:
   a first, central layer of a single strand;
   a second layer of six strands;
   a third layer of twelve strands; and
   a fourth, outermost layer of eighteen strands,
   the wire filaments each having a diameter between 0.005 mm and 0.143 mm, and the wire cable having an outermost diameter between 0.11 mm and 3.0 mm; and
   wherein at least the third and fourth layers are wound in mutually opposite helical directions.

13. The wire cable of claim 12, wherein the wire filaments are made of a metallic material selected from the group consisting of stainless steel, tungsten, and cobalt chromium alloys.

14. The wire cable of claim 13, wherein the wire filaments are all made from the same metallic material.

15. The wire cable of claim 14, wherein the wire filaments are all formed with a common diameter.

16. The wire cable of claim 12, wherein each strand includes 19 of the wire filaments.

17. The wire cable of claim 16, wherein the diameters of the wire filaments are between 0.005 mm and 0.086 mm.

18. The wire cable of claim 12, wherein each strand includes 37 of the wire filaments.

19. The wire cable of claim 18, wherein the diameters of the wire filaments are between 0.005 mm and 0.061 mm.

20. The wire cable of claim 12, wherein each of the wire filaments comprise tungsten.

21. The wire cable of claim 12, wherein each of the wire filaments comprise stainless steel.

22. A medical device, comprising:
at least one pulley having a root diameter; and
a wire cable comprising:
37 strands, each strand including at least 7 wire filaments, the strands arranged in layers comprising:
a first, central layer of a single strand;
a second layer of six strands;
a third layer of twelve strands; and
a fourth, outermost layer of eighteen strands,
the wire cable having an outermost diameter between 0.11 mm and 3 mm, and the root diameter being between 3 and 6 times the outermost diameter of the wire cable; and
wherein a lay factor of each of the first through fourth layers is between 5 and 17.

23. The medical device of claim 22, wherein the root diameter is between 1 mm and 6 mm.

24. The medical device of claim 22, wherein the wire filaments each have a diameter between 0.005 mm and 0.14 mm.

25. The medical device of claim 22, wherein the wire filaments are made of a metallic material selected from the group consisting of stainless steel, tungsten, and cobalt chromium alloys.

26. The medical device of claim 25, wherein the wire filaments are all made from the same metallic material.

27. The medical device of claim 26, wherein the wire filaments are all formed with a common diameter.

28. The medical device of claim 22, wherein each strand includes 19 of the wire filaments.

29. The medical device of claim 28, wherein the wire filaments each have a diameter between 0.005 mm and 0.086 mm.

30. The medical device of claim 22, wherein each strand includes 37 of the wire filaments.

31. The medical device of claim 30, wherein the wire filaments each have a diameter between 0.005 mm and 0.061 mm.

32. The medical device of claim 22, wherein:
the lay factor of the first layer is between 7 and 17;
the lay factor of the second layer is between 5 and 13;
the lay factor of the third layer is between 6 and 15; and
the lay factor of the fourth layer is between 6 and 15.

33. The medical device of claim 22, wherein each of the wire filaments comprise tungsten.

34. The medical device of claim 22, wherein each of the wire filaments comprise stainless steel.

35. A medical device, comprising:
at least one pulley having a root diameter; and
a wire cable comprising:
37 strands, each strand including at least 7 wire filaments, the strands arranged in layers comprising:
a first, central layer of a single strand;
a second layer of six strands;
a third layer of twelve strands; and
a fourth, outermost layer of eighteen strands,
the wire cable having an outermost diameter between 0.11 mm and 3 mm, and the root diameter being between 3 and 6 times the outermost diameter of the wire cable; and
wherein at least the third and fourth layers are wound in mutually opposite helical directions.

36. The medical device of claim 35, wherein each of the wire filaments comprise tungsten.

37. The medical device of claim 35, wherein each of the wire filaments comprise stainless steel.

* * * * *